April 4, 1967 J. C. MIKKELSEN Plant Pat. 2,731
POINSETTIA PLANT
Filed Feb. 25, 1966
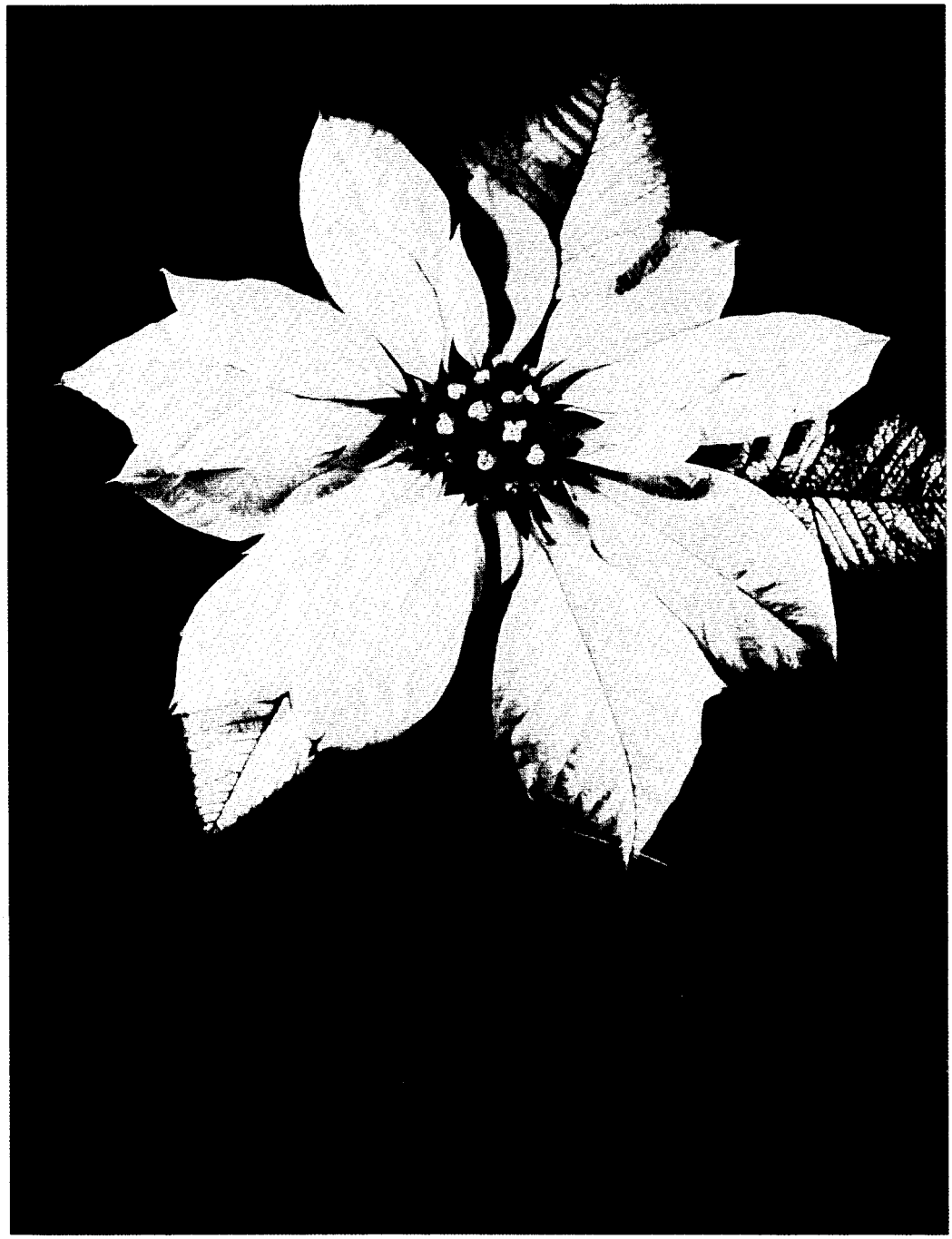
Inventor.
J. C. Mikkelsen
By: Robb & Robb
Attorneys.

United States Patent Office

Plant Pat. 2,731

Patented Apr. 4, 1967

2,731

POINSETTIA PLANT

James C. Mikkelsen, 1803 W. 13th St., Ashtabula, Ohio 44004

Filed Feb. 25, 1966, Ser. No. 530,238

1 Claim. (Cl. Plt.—86)

The present invention relates to a new and distinct variety of poinsettia plant which was discovered by me in my greenhouse at Ashtabula, Ohio, as a mutation or sport of the variegated pink and white variety known as "Mikkeldawn" (plant patent pending).

In the course of my development and propagation of the variety "Mikkeldawn," which as discovered by me as a mutation of the variety "Mikkelpink" (Plant Patent No. 2,501), I found among the plants of "Mikkeldawn" an occasional plant which would have from one to several all-white bracts, and also one plant completely having white bracts without any trace of pink coloration. After further development and tests of these latter plants and progeny thereof derived from cuttings taken therefrom and asexually reproduced by me at Ashtabula, Ohio, I concluded that plants having all-white bracts could be successfully reproduced and would come true, as proved by the plants reproduced by me at Ashtabula from the cuttings aforementioned.

Except for the all-white bracts, my new poinsettia variety has the same overall general characteristics as the variety "Mikkeldawn" and represents a new and distinct combination of the following features which are outstanding therein and which distinguish it from all other poinsettia varieties of which I am aware:

(1) A semi-dwarf habit of growth;

(2) Rigid and upright stems which do not require staking and which are ideal for short, compact and long-lasting plants which are particularly suitable for home decorations;

(3) Relatively small flower buds which do not drop excessive pollen or nectar;

(4) A distinctive and attractive light cream-white coloration of the bracts which make the plants especially desirable for decorative purposes;

(5) A non-drooping habit of the bracts with age;

(6) Excellent keeping qualities without exacting growing techniques to prevent early flowering; and (7) Good shipping qualities attributable to the semi-dwarf habit, rigid stems and short leaves and bracts which are less susceptible to damage or injury during shipping than most other commercial varieties.

The accompanying drawing shows a typical specimen plant of my new poinsettia variety as depicted in color as nearly true as it is reasonably possible to make the same in a color illustration of this character.

The following is a detailed description of my new poinsettia variety, with color terminology in accordance with Wilson's Horticultural Colour Chart, except where general color terms of ordinary dictionary significance are obvious, as based on specimens grown at Ashtabula, Ohio, under regular commercial practices:

Parentage: Sport of "Mikkeldawn."

Form: Semi-dwarf; compact; upright; no branching.

Habit of growth: Slower than present commercial varieties; no self-branching.

Rooting habit: Substantially identical to that of the antecedent variety "Paul Mikkelsen" (Plant Patent No. 2,328); roots are quite fibrous and are less susceptible to root rot organisms that other present commercial varieties, as determined by comparison with other varieties grown under comparable conditions at Ashtabula, Ohio.

Blooming habit: Normal.

Blooming season: Late November and December; very suitable for forcing.

Foliage: Alternate on stems; borne on stems at a slight upward angle ranging from about 15° to 20°; foliage does not tend to fall off as the plant matures or when subjected to sudden environmental changes.

*Size.*—Medium (from about 4 inches to 6 inches long) when grown with good fertilizing practices.

*Quantity.*—Above normal.

*Texture.*—Upper side—becomes semi-glossy at maturity; veins have definite recessed and dendritic pattern. Under side—veins have definite protrusion.

*Margin.*—Clean-cut and distinct.

*Color.*—New foliage—upper side: Sap Green, Plate 62, page 62, when about ½ inch to ¾ inch long, changing to Pod Green, Plate 061, page 120, when leaf is about 2 inches to 3 inches long. Under side: Pod Green, Plate 061/1, page 120. Old foliage—upper side: Spinach Green, Plate 0960, page 187. Under side: Spinach Green, Plate 0960/2, page 187. Petiole—Color: Light Green; has no Pink coloration as in "Mikkelpink" or Red coloration as in "Paul Mikkelsen".

Disease resistance: Resistant to botrytis and mildew, as determined by comparison with other varieties grown under the same cultural conditions at Ashtabula, Ohio, which were infected with these diseases.

Bracts: Become more long-pointed as cyathia develop; bract development continues over a much longer period of time than in other White poinsettia varieties, and bracts retain a horizontal position for many months; bracts have a slight twisting formation at the very tip end. Color—Light Cream-White.

Flowers:

*Borne.*—Continuously for several months, with many cyathia to a stem in regular clusters in varying stages of development; borne on short, strong stems.

*Quantity of bloom.*—Relatively abundant; continuous during one season of 3 to 4 months.

*Cyathia.*—Small; borne on Light Green stems corresponding to the same color as the main stem of the plant in that area; cyathia drop off gradually after maturity, but new ones continue to develop as the flowering stems continue to develop. Color—Scheele's Green. Plate 860/1, page 175, with outer areas of the cyathia turning to Lemon Yellow, Plate 4/1, page 4, instead of Red as in the "Paul Mikkelsen" and "Mikkelpink" varieties and constituting a significant difference.

Reproductive organs:

*Stamens.*—Quite numerous; from ⅛ inch to ¼ inch long. Color—colorless in early stages, but turning to Cream-White when stamens drop.

*Pollen.*—Color—Canary Yellow, Plate 2, page 2.

*Styles.*—Color—Cream-White, turning to Pinkish or dirty White at maturity.

*Ovaries.*—Color—Scheele's Green, Plate 860/1, page 175.

*Nectar cups.*—Color—Lemon Yellow, Plate 4/1, page 4.

*General observations*

My new variety is a significant contribution to the poinsettia industry in that it adds the White type having the same over-all characteristics as the varieties "Paul Mikkelsen" and "Mikkelpink," and allowing growers to have the full range of colors growing under the same cultural conditions, while also allowing the grower to make attractive combinations of Red and White, or Pink and White flowering plants in the same pot. with uniform height from the beginning of the planting until flowering occurs. The new variety is distinctly different from the leading commercial White varieties known as "Ecke's White" (Plant Patent No. 1,802) and "New Ecke's White" (unpatented) by virtue of being more rigid and upright and therefore not as wild or limp as those other varieties, with shorter and broader leaves, and the bracts of my new variety are Whiter in color, with very little Chartreuse coloration being present, thereby achieving an over-all clean White effect which is more attractive and useful. The bracts of my new variety are also shorter and broader than those of "Eck'e White," but are equally numerous, more rigid and more permanent, with both the foliage and the bracts being maintained on the plant longer even under severe conditions. Generally, there is less nectar and pollen on the flowers of my new variety than in the variety "Ecke's White," and the new variety ships and handles better.

I claim:

A new and distinct variety of poinsettia plant, substantially as herein shown and described, characterized particularly as to novelty by the unique combination of a semi-dwarf habit of growth, rigid and upright stems which do not require staking and which are ideal for short, compact and long-lasting plants which are particularly suitable for home decorations, relatively small flower buds which do not drop excessive pollen or nectar, a distinctive and attractive light cream-white coloration of the bracts which make the plants especially desirable for decorative purposes, a non-drooping habit of the bracts with age, excellent keeping qualities without exacting growing techniques to prevent early flowering, and good shipping qualities attributable to the semi-dwarf habit, rigid stems and short leaves and bracts which are less susceptible to damage or injury during shipping than most other commercial varieties.

No references cited.

ABRAHAM G. STONE, *Primary Examiner.*

ROBERT E. BAGWILL, *Examiner.*